US009103820B2

(12) United States Patent
Nishikawa

(10) Patent No.: US 9,103,820 B2
(45) Date of Patent: Aug. 11, 2015

(54) METHOD FOR SCREENING TOXIN NEUTRALIZING PEPTIDE, STX2 INHIBITING PEPTIDE AND VEROTOXIN NEUTRALIZING AGENT

(75) Inventor: Kiyotaka Nishikawa, Tokyo (JP)

(73) Assignee: JAPAN SCIENCE AND TECHNOLOGY AGENCY, Kawaguchi-shi, Saitama (JP)

( * ) Notice: Subject to any disclaimer, the term of this patent is extended or adjusted under 35 U.S.C. 154(b) by 1774 days.

(21) Appl. No.: 11/631,008

(22) PCT Filed: Jun. 28, 2005

(86) PCT No.: PCT/JP2005/012286
§ 371 (c)(1),
(2), (4) Date: Jan. 30, 2008

(87) PCT Pub. No.: WO2006/001542
PCT Pub. Date: Jan. 5, 2006

(65) Prior Publication Data
US 2009/0029864 A1    Jan. 29, 2009

(30) Foreign Application Priority Data

Jun. 28, 2004  (JP) ................................. 2004-189801
Oct. 7, 2004   (JP) ................................. 2004-295405

(51) Int. Cl.
| C40B 30/04 | (2006.01) |
| C07K 7/00 | (2006.01) |
| G01N 33/50 | (2006.01) |
| A61K 38/00 | (2006.01) |

(52) U.S. Cl.
CPC ............ *G01N 33/5014* (2013.01); *A61K 38/00* (2013.01)

(58) Field of Classification Search
CPC .................................. C40B 30/04; C07K 7/00
USPC ........................................................ 506/7, 9
See application file for complete search history.

(56) References Cited

U.S. PATENT DOCUMENTS

| 6,417,423 B1 * | 7/2002 | Koper et al. ................... 588/313 |
| 7,208,293 B2 * | 4/2007 | Ladner et al. ................. 435/69.7 |
| 7,422,740 B1 * | 9/2008 | Purdy et al. ................. 424/133.1 |
| 7,576,183 B2 * | 8/2009 | Gupta et al. ................. 530/387.1 |
| 7,625,559 B2 * | 12/2009 | Ambrosino et al. ........ 424/139.1 |
| 7,674,470 B2 * | 3/2010 | Shone et al. ................. 424/247.1 |
| 2003/0113717 A1 * | 6/2003 | Ladner et al. ..................... 435/6 |

FOREIGN PATENT DOCUMENTS

| JP | 11-199491 | * 7/1999 | ............. A61K 35/16 |
| JP | 2004-350686 | 12/2004 | |
| WO | WO 9323425 A1 | * 11/1993 | |

OTHER PUBLICATIONS

Nishikawa et al., A Therapeutic Agent With Oriented Carbohydrates for Treatment of Infections by Shiga Toxin-Producing *Escherichia coli* 0157:H7, Proceedings of the National Academy of Sciences, 99(11), 7669-7674.*

Kitov et al., Shig-like Toxins Are Neutralized By Tailored Multivalent Carbohydrate Ligands, Nature, 2000, 403, 669-672.*

Pavel I. Kitov et al., "Shiga-like toxins are neutralized by tailored multivalent carbohydrate ligands", Nature, Nature Publishing Group, vol. 403, Feb. 10, 2000, pp. 669-672.

Miho Watanabe et al., "Oral therapeutic agents with highly clustered globotriose for treatment of shiga toxigenic *Escherichia coli* infections", The Journal of Infectious Disease, Feb. 1, 2004, vol. 189, No. 3, pp. 360-368.

Zhou Songyang et al., "Use of an oriented peptide library to determine the optimal substrates of protein kinases", Current Biology, Current Science, GB, vol. 4, No. 11, Nov. 1, 1994, pp. 973-982.

* cited by examiner

*Primary Examiner* — Maria Leavitt
*Assistant Examiner* — Amy M Bunker
(74) *Attorney, Agent, or Firm* — Wenderoth, Lind & Ponack, L.L.P.

(57) ABSTRACT

A screening method directed towards; (1) specifying a receptor binding site by introduction of mutation, and (2) specifying a binding site-specific peptide motif on the basis of an amino acid selection ratio by contrast between a peptide motif bound to a wild-type subunit and a peptide motif bound to a mutant functionally deficient in the binding site according to a peptide library method. A peptide which inhibits a toxin whose receptor binding portion has a subunit structure is screened. Accordingly, an STX2 inhibitor in which an STX2 inhibiting peptide is incorporated in a molecular nuclear structure portion having three molecules of lysine (Lys) peptide-linked thereto and which is easy to synthesize and can inhibit verotoxin is provided.

4 Claims, 7 Drawing Sheets

METHOD FOR SCREENING TOXIN NEUTRALIZING PEPTIDE, STX2 INHIBITING PEPTIDE AND VEROTOXIN NEUTRALIZING AGENT

This application is the U.S. National Stage of PCT/JP2005/012286 filed Jun. 28, 2005 which claims priority to JP2004-189801 filed Jun. 28, 2004 and JP2004-295405 filed Oct. 7, 2004.

TECHNICAL FIELD

This invention relates to a method for screening a toxin neutralizing peptide which can inhibit toxins such as verotoxin, cholera toxin and pertussis toxin.

This invention further relates to an STX2 inhibiting peptide and a verotoxin neutralizing agent. More specifically, it relates to an STX2 inhibiting peptide which can competitively inhibit adhesion of verotoxin to cells to effectively inhibit the verotoxin, and a verotoxin neutralizing agent capable of oral administration.

BACKGROUND ART

Verotoxins that enterohemorrhagic *Escherichia coli* O157:H7 produces are proteins belonging to the $AB_5$ family of bacterial toxins analogous to Shiga toxin derived from dysentery *bacillus*, and it has been known that these toxins are incorporated into cells by recognizing and bonding a globo3 sugar moiety of globotriaosylceramide ($Gb_3$, Galα1-4Galβ1-4G1cβ1-Cer) in vascular endothelial cells of various target organs to show a toxicity.

Such Shiga-like toxins include two types, and these toxins induce hemorrhagic colitis, severe complications as a series of consequential microvascular disorders [for example, hemolytic uremic syndrome (HUS)] and the like. A toxin expressed as STX1 has the same amino acid sequence as Shiga toxin produced by *Shigella dysenteriae* [*Shigella dysenteriae* Type I). Meanwhile, a toxin expressed as STX2 has an amino acid sequence which is identified to be homologous to that of STX1 by 50 to 60%. Although there is a slight difference in amino acid sequence, toxicities thereof show activities such as a cytotoxicity and an intestinal toxicity by inhibition of protein synthesis. STX is an $AB_5$-type toxin comprising two types of subunits (A and B) in which one molecule of A-subunit is surrounded by five molecules of B-subunit via hydrophobic binding. It is A-subunit that plays a roll in toxicity, and B-subunit plays a roll in binding to a sugar chain receptor present on the surface of the cell. Through detailed examination by analysis of X-ray crystal structure of the toxin, it has been clarified that three binding sites of a sugar chain are present in one molecule of B-subunit. That is, since five molecules of B-subunit are present in STX2 of one molecule, it is presumed that 15 binding sites in total are presented.

That is, STX is classified in two families, STX1 and STX2. It is mainly STX2 producing bacteria that induce severe complications, and STX2 is more significant clinically. For this reason, the development of an inhibitor of STX2 is urgently required. These STXs are $A-B_5$-type toxins, and incorporated into cells such that B-subunit is bound to $Gb_3$ (globotriaosylceramide: Galα(1-4)-Galβ(1-4)-Galcβ1-Ceramide), a receptor on the cell membrane. A B-subunit pentamer specifically recognizes a Gb3 sugar chain moiety (globo3 sugar: Galα(1-4)-Galβ(1-4)-G1cβ1-). Accordingly, a compound in which globo3 sugar is accumulated at high density is bound to STX with high affinity, and becomes an STX inhibitor of inhibiting its function.

Since the subunit structure of the toxin and its function have been clarified, a method for selectively inhibiting the binding of B-subunit having a function of binding to the sugar chain receptor on the cell surface has attracted much interest, and studies thereof have been made from various aspects.

The inventors of this application have also conducted construction of an artificial sugar chain cluster which effectively binds the sugar chain to the sugar chain binding site of the toxin to inhibit the adhesion of the toxin to the host cell. They have so far proposed a dendrimer compound group having carbosilane as a sugar chain-supporting structure or water-soluble polymer compounds (Patent Documents 1 and 2, and non-Patent Document 1).

Examples thereof include SUPER TWIG (1)6 represented by the following formula, and the like. This is the first compound whose effectiveness has been verified in an O157:H7 infection experiment.

The past development of STX inhibitors including SUPER TWIG has been conducted on the basis of the concept of how the globo3 sugar as an STX-binding unit is accumulated for exhibiting an inhibitory activity in vivo. However, an affinity (Kd) for STX with the globo3 sugar alone is $10^{-3}$ M which is not necessarily high, and its chemical synthesis is quite difficult. This is a great barrier to clinical application. Accordingly, for the development of clinically applicable therapeutic agents, the development of a new STX-binding unit which is easier to synthesize than the globo3 sugar and excellent in bindability to STX is required.

Further, it is presumed that the foregoing problem is not only peculiar to the verotoxin but also common to, other than the verotoxin STX, cholera toxin (A-B5 type) receptor: GM1, enterotoxigenic *Escherichia coli* heat-labile diarrhea causal toxin LT (A-B5 type) receptor: GM1, pertussis toxin (A-B5 type) receptor, *Bacillus anthracis* toxin (heptamer type) receptor: protein having VWA domain (anthrax toxin receptor) in which a receptor binding portion is considered to have a subunit structure, and the like.

Under these circumstances, the inventors of this application have conducted investigations to construct a substance formulated as a receptor of these toxins.

Patent Document 1: WO 02/02588
Patent Document 2: Japanese Patent Application No. 2004-108483
Non-Patent Document 1: Proc. Natl. Acad. Sci. USA 2002; 99; 7669-74

DISCLOSURE OF THE INVENTION

Under these circumstances, on the basis of the studies which have been so far conducted by the inventors, this invention aims to provide a new screening method for realizing a toxin neutralizing agent which is easy to synthesize and can effectively inhibit a toxin whose receptor binding portion has a subunit structure, such as verotoxin.

Further, on the basis of the studies which have been so far conducted by the inventors, this invention aims to provide a new STX inhibitor which is easy to synthesize and can effectively inhibit verotoxin, namely a verotoxin neutralizing agent.

For solving the foregoing problems, the inventors of this application have conducted studies on a possibility of realizing toxin neutralizing peptides. Attention has been drawn to peptides mainly because synthesis thereof is relatively easy and a safety is generally high in application to drugs.

As a result of the assiduous investigations by the inventors, this application is to provide first, for solving the foregoing problems, the following method for screening a toxin neutralizing peptide, and more specifically to provide an STX2 inhibiting peptide and a verotoxin neutralizing agent.

1st: A method for screening a toxin neutralizing peptide which can neutralize a toxin whose receptor binding portion has plural subunit structures, comprising the following steps;
(1) specifying a receptor binding site by introduction of mutation, and
(2) specifying a binding site-specific peptide motif on the basis of an amino acid selection ratio by contrast between a peptide motif bound to a wild-type subunit and a peptide motif bound to a mutant functionally deficient in the binding site according to a peptide library method.

2nd: The method for screening the toxin neutralizing peptide, wherein the step (2) is conducted plural times to specify the binding site-specific peptide motif having the higher amino acid selection ratio in order.

3rd: The method for screening the toxin neutralizing peptide, wherein in the step (2), a 1st polyvalent peptide library is used in which a nuclear structure having plural lysines (Lys) bound thereto is formed and plural peptide libraries are bound to the terminal amino acid thereof.

4th: The method for screening the toxin neutralizing peptide, wherein in the 1st polyvalent peptide library, the peptide library is bound to the terminal amino group via a spacer molecule.

5th: An STX2 inhibiting peptide in which a peptide motif which is formed by peptide linkage of at least seven amino acids, whose sequence has two cluster portions each having at least two basic amino acids bound thereto and whose C-terminal side is a basic amino acid is incorporated in a molecular nuclear structure portion having three molecules of lysine (Lys) peptide-linked thereto.

6th: The STX2 inhibiting peptide, wherein at least arginine (Arg) is contained as the basic amino acid of the cluster portion.

7th: The STX2 inhibiting peptide, wherein the cluster portion is Arg-Arg or Arg-Arg-Asn.

8th: The STX2 inhibiting peptide, wherein the N-terminal side is a hydrophobic amino acid.

9th: The STX2 inhibiting peptide, wherein any of peptide motifs of the following four amino acid sequences is incorporated in the molecular nuclear structure portion having the three molecules of lysine (Lys) peptide-linked thereto.

(1) FRRNRRN (SEQ ID NO: 1)
(2) PPPRRRR (SEQ ID NO: 2)
(3) PPRRNRR (SEQ ID NO: 3)
(4) KRRNPRR (SEQ ID NO: 4)

10th: The STX2 inhibiting peptide, wherein the peptide motif is incorporated via a spacer molecule.

11th: The STX2 inhibiting peptide, wherein the spacer molecule is a molecule having a peptide or an amino group and a carboxyl group and having a hydrocarbon chain structure with from 4 to 10 carbon atoms.

12th: The STX2 inhibiting peptide, wherein the peptide motif has a terminal modification molecule.

13th: The STX2 inhibiting peptide, wherein the terminal modification molecule is an uncharged molecule.

14th: The STX2 inhibiting peptide, wherein the peptide motif may have a molecule for amino acid sequencing.

15th: The STX2 inhibiting peptide represented by the following formula (a) or (b), $$(\text{Met-Ala-Xo-Ala-AHA-})_4\text{-3Lys} \quad (a)$$

$$(\text{acetyl-Xo-AHA-})_4\text{-3Lys} \quad (b)$$

[wherein AHA represents an aminohexanecarboxylic acid group, Xo represents any of the foregoing peptide motifs (1), (2), (3) and (4), and 3Lys represents a structure of the following formula (1)

$$\begin{array}{c}
-\text{NH} \\ \phantom{-}\diagdown \\ \phantom{--}(CH_2)_4 \\ \phantom{---}\diagdown \\ \phantom{----}CH-CONH-CH-(CH_2)_4-NHCO-CH \\ \phantom{---}\diagup \phantom{-------------}| \phantom{-------------}\diagdown \\ -\text{NH} \phantom{------------}CO \phantom{-------------}\text{NH}- \\ \phantom{------------------}| \\ \phantom{------------------}OH \\ \phantom{-------------------}\diagup \\ \phantom{----------------}(CH_2)_4 \\ \phantom{----------------}\diagup \\ \phantom{---------------}\text{NH}-
\end{array}$$

16th: A verotoxin neutralizing agent comprising the foregoing peptide as an active ingredient.

BEST MODE FOR CARRYING OUT THE INVENTION

Figure 1:
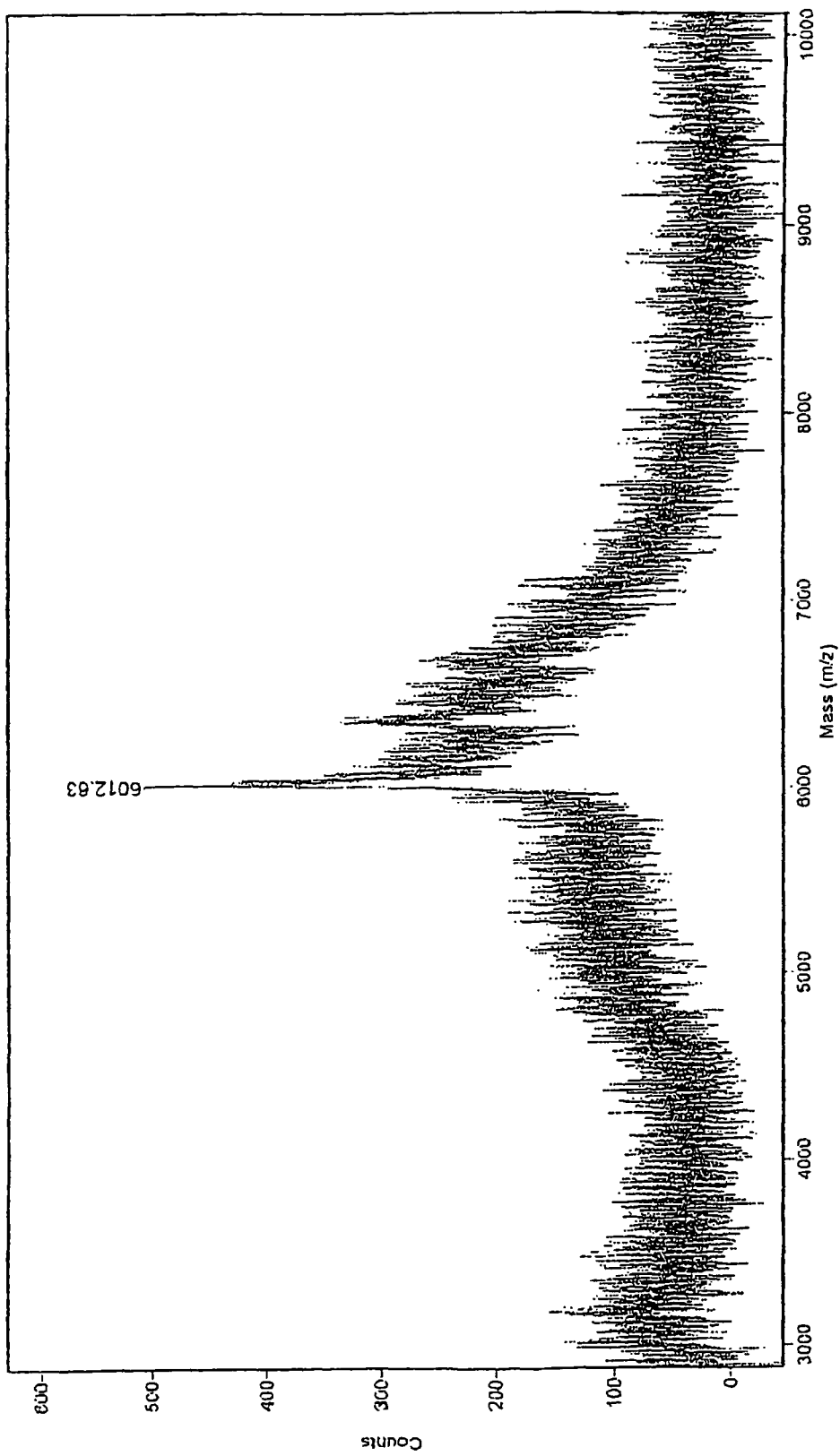
FIG. 1 is a mass spectrum of a compound of peptide motif (1) FRRNRRN (SEQ ID NO: 1).
Figure 2:
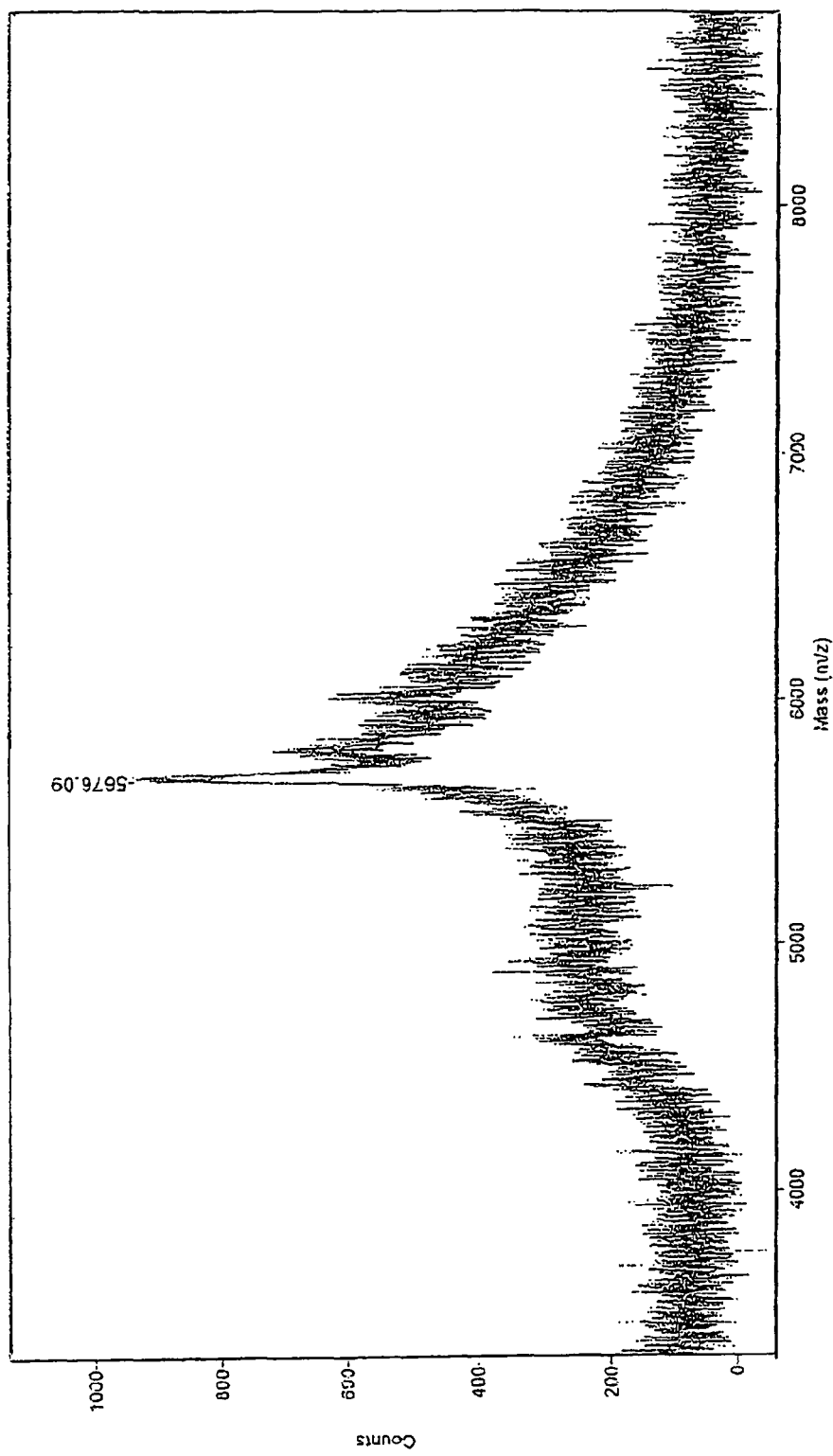
FIG. 2 is a mass spectrum of a compound of peptide motif (2) PPPRRRR (SEQ ID NO: 2).
Figure 3:
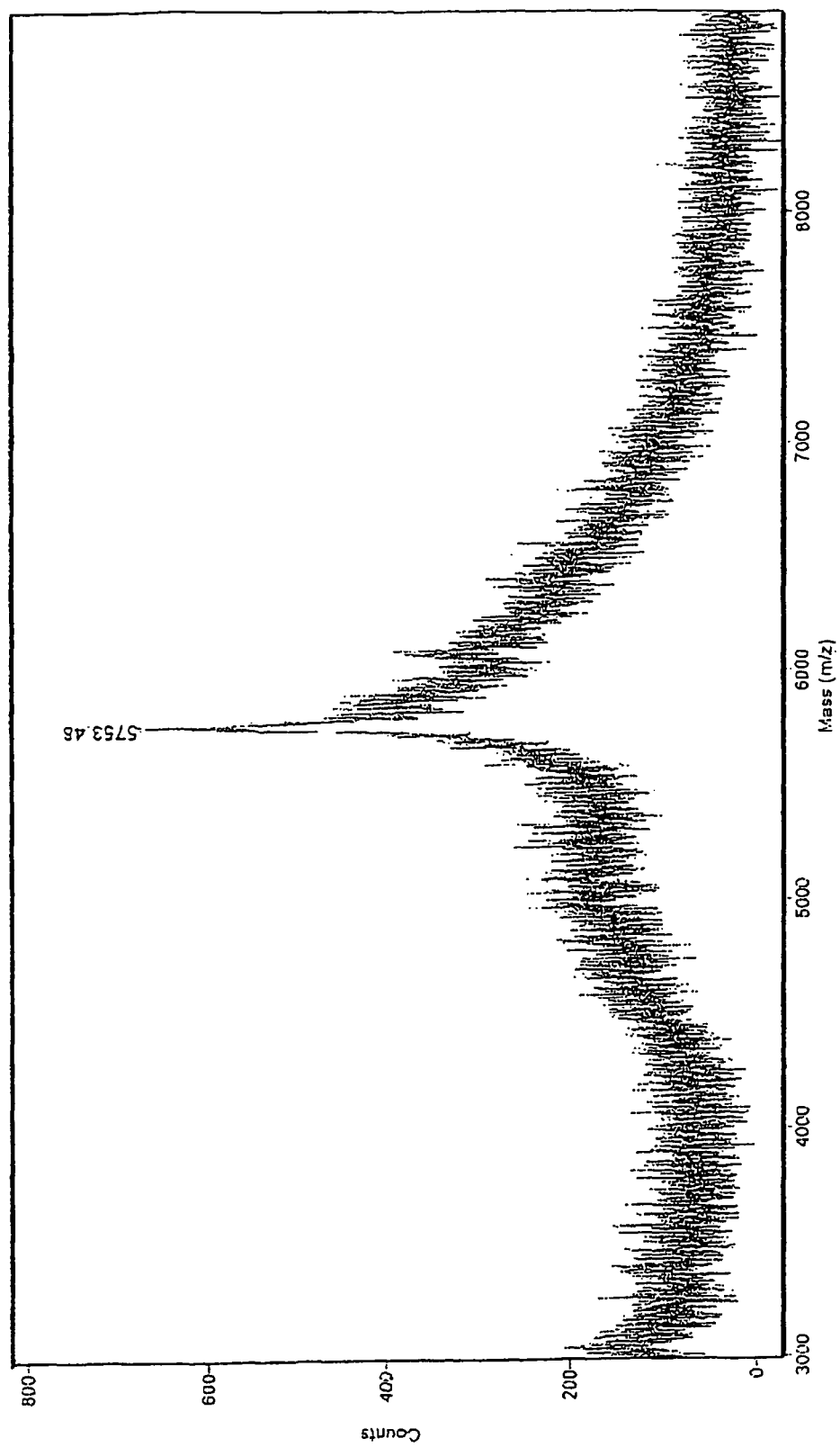
FIG. 3 is a mass spectrum of a compound of peptide motif (3) PPRRNRR (SEQ ID NO: 3).
Figure 4:
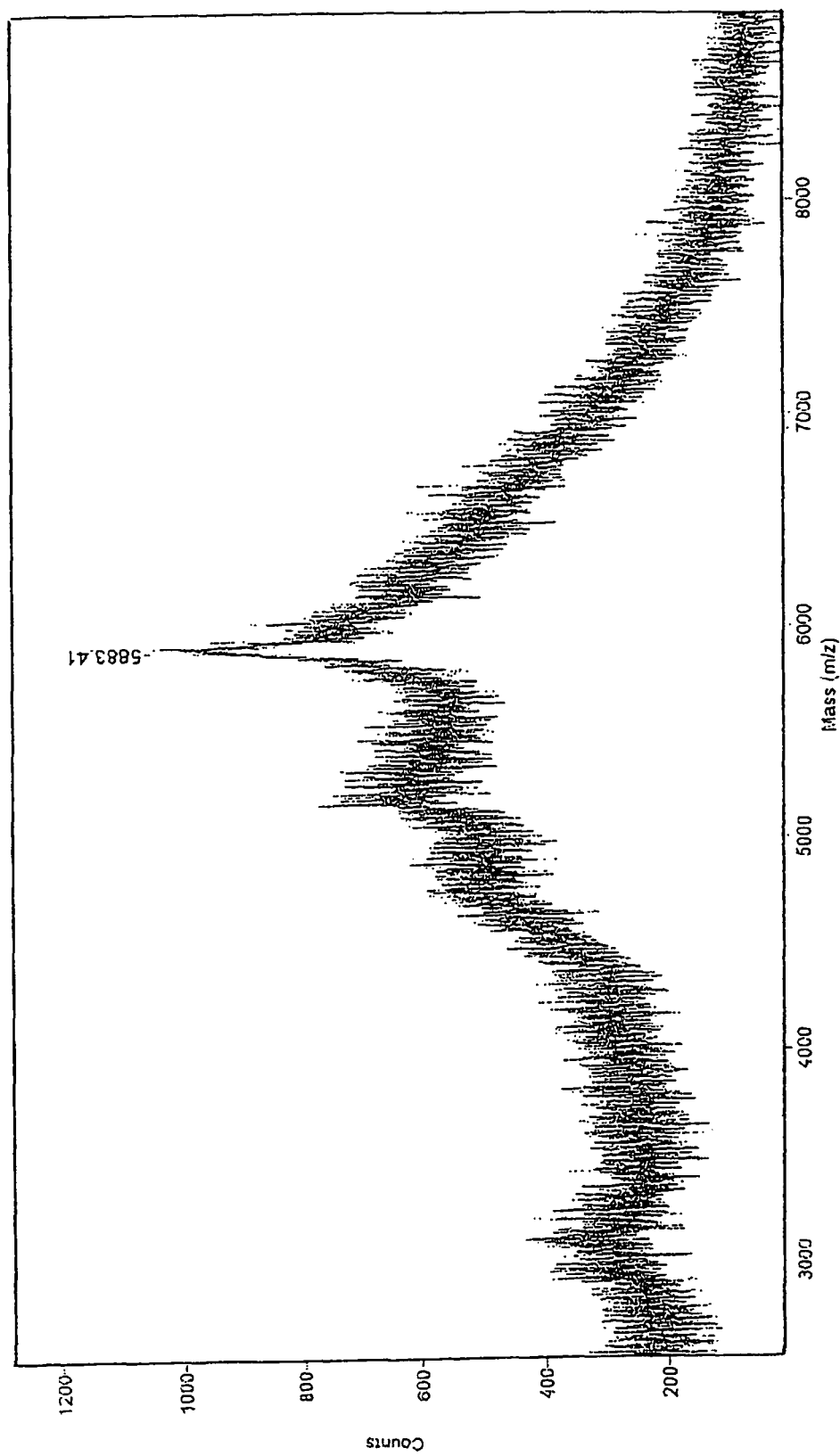
FIG. 4 is a mass spectrum of a compound of peptide motif (4) KRRNPRR (SEQ ID NO: 4).

The invention has the foregoing characteristics, and the embodiments thereof are described below.

<Screening of a Toxin Neutralizing Peptide>

First, basically, the method for screening the toxin neutralizing peptide in this invention comprises, as described in the first invention, the following steps;

(1) specifying a receptor binding site by introduction of mutation, and (2) specifying a binding site-specific peptide motif on the basis of an amino acid selection ratio by contrast between a peptide motif bound to a wild-type subunit and a peptide motif bound to a mutant functionally deficient in the binding site according to a peptide library method.

As a preferable embodiment, it is considered that the step (2) is conducted plural times to specify the binding site-specific peptide motif having the higher amino acid selection ratio in order.

Since the knowledge is obtained that a cluster effect exists in the binding between the subunit and the receptor, it is advisable that an initial (1st) peptide library for the step (2) has a nuclear structure formed by binding plural amino acids to comply with the cluster effect.

With respect to such a nuclear structure, from the aspects of, for example, its designing, easiness of its synthesis and, among others, a molecular size for an actual cluster effect, it is considered that a nuclear structure having bound thereto plural lysines (Lys), for example, preferably from 2 to 5 lysines is used and a peptide library itself is polyvalent.

That is, in the step (2), a 1st polyvalent peptide library is used in which a nuclear structure having plural lysines (Lys) bound thereto is formed and plural peptide libraries are bound to the terminal amino acid thereof. In the 1st polyvalent peptide library, the peptide library may be bound to the terminal amino group via a spacer molecule. In this case, it is indicated as a preferable example that, for example, the spacer molecule is a molecule having a peptide or an amino group and a carboxyl group and having a hydrocarbon chain structure with from 4 to 10 carbon atoms.

The receptor binding site in the step (1) may be a known site or may be specified as a site in which mutation is actually introduced to have a great influence on the binding to the receptor. According to the inventors of this application, in verotoxin STX, the binding site of the receptor has been already found to be specified in the binding of globo3 sugar.

<Screening of a Verotoxin Neutralizing Peptide and an STX2 Inhibiting Peptide>

Accordingly, the invention is described in more detail below by referring to an example of screening a verotoxin inhibiting peptide.

Infection of enterohemorrhagic *Escherichia coli* such as O157:H7 not only induces hemorrhagic colitis but also sometimes accompanies hemolytic uremic syndrome (HUS) and encephalopathy, and these complications rather become serious causes to bring patients to death. The verotoxin (Shiga toxin: STX) is a main pathogenic factor produced by enterohemorrhagic *Escherichia coli*, and a microvascular endothelium disorder of kidneys or brain due to verotoxin invaded into the blood is considered to cause the complications. Accordingly, an STX absorbing agent which strongly absorbs STX produced in the intestinal tract to inhibit the invasion of STX into the blood and an STX neutralizing agent which is bound to a trace amount of STX already invaded into the blood to inhibit its function have been expected as effective therapeutic agents of infectious diseases of enterohemorrhagic *Escherichia coli*.

The screening of the *Escherichia coli* verotoxin neutralizing peptide can be based on the inventors' detailed investigations on the relation between the molecular structure of SUPER TWIG (1)6 and the functional mechanism thereof.

The detailed description is as follows.

1) Identification of binding sites of STX1B- and 2B-subunits of SUPER TWIG (1)6

Three types of globo3 sugar binding sites called sites 1, 2 and 3 exist in one B-subunit monomer. Accordingly, it is known that fifteen globo3 sugars in total can be bound to a B-subunit pentamer. For developing a new STX binding unit, what site is targeted is first a serious problem. Therefore, single, double and triple mutations were introduced in the respective sites to prepare various mutant B-subunits, and binding affinities between these mutants and SUPER TWIG (1)6 were comparatively examined. Consequently, it was found that "sites 1 and 2" or "site 3 alone" are/is used in the binding between SUPER TWIG (1)6 and STX 1B-subunit and that "site 3 alone" is used in the binding between SUPER TWIG (1)6 and STX2B-subunit. That is, for developing a new binding unit to STX2 which is clinically more significant, it was found that site 3 may be targeted.

2) Development of a New STX Binding Unit

In consideration of the clinical significance and the specificity of the binding site clarified in (1), a new substance which can be bound to STX2B-subunit to inhibit the toxicity of STX2 has been decided to be investigated as a substance having a peptide structure. Attention has been drawn to this peptide mainly because its synthesis is relatively easy, it is generally applied as a drug without a great barrier and there is a strong possibility of the development of its variation and derivatives.

In search of the active peptide from these aspects, peptide libraries have been newly developed.

That is, on the basis of the findings obtained in 1), a binding motif specific to site 3 of STX2B-subunit has been determined by subtracting a peptide motif bound to mutant STX2B-subunit functionally deficient in site 3 from a peptide motif bound to wild-type STX2B-subunit.

That is, first, the inventors have already developed a peptide library method which is a method for determining a motif directly bound to a functional domain such as a catalytic site of a protein kinase (K. Nishikawa et al., Mol. Cell, 6, 969-2000). Thus, on the basis of the knowledge of this peptide library method, a peptide library based on a new concept that a peptide library per se is polyvalent has been developed using the fact that a cluster effect exists in the binding of the B-subunit pentamer and the globo3 sugars in the verotoxin neutralizing agent as described above.

First, in consideration of the size and the like of the nuclear molecule structure in the foregoing SUPER TWIG (1)6, a compound in which four peptide libraries are bound via spacers has been synthesized using a structure having three lysines (Lys) bound thereto as represented by the following formula $$\begin{array}{c}
\text{—NH} \\
\phantom{x}\backslash \\
(CH_2)_4 \\
\phantom{x}\backslash \\
\text{CH—CONH—CH—}(CH_2)_4\text{—NHCO—CH} \\
\phantom{x}/\phantom{xxxxxxxxxx}|\phantom{xxxxxxxxxxxxxxxxx}\backslash \\
\text{—NH}\phantom{xxxxxxxx}CO\phantom{xxxxxxxxxxxxx}\text{NH—} \\
\phantom{xxxxxxxxxxxx}| \\
\phantom{xxxxxxxxxxxx}OH
\end{array}
\begin{array}{c}
\text{NH—} \\
/ \\
(CH_2)_4 \\
/ \\
\\
\\
\end{array}$$

as a nuclear structure used for making the peptide library polyvalent. This compound is one in which four peptide libraries (Xaa-Xaa-Xaa-Xaa) represented by the following formula

MAXXXXA-AHA-        (SEQ ID NO: 5)

are bound to a terminal amino group in the Lys nuclear molecule structure in the foregoing formula, namely (MAXXXXA-AHA)$_4$-3Lys. In this compound, AHA in the formula indicates aminohexanoic acid constituting the spacer molecule.

AHA (aminohexanoic acid) has a length of 6 carbon atoms, and it is used to comply with the optimum conditions of SUPER TWIG. Terminal MA (Met-Ala) is introduced at the time of screening for checking whether the amino acid sequencing is surely conducted in the sequencing. A (Ala) before AHA- is also introduced for the same reason. The designing is performed to comply with the optimum structure of SUPER TWIG in all of its shape, a distance between branched chains present in the nuclear structure, a valence of the library and a distance between the libraries. When the resulting compound was subjected to the amino acid sequencing, it could be confirmed that 19 types of amino acids (except Cys) used were efficiently randomized in positions where the amino acids were degenerated.

Upon using this 1st peptide library, a peptide motif bound to wild-type STX2B-subunit was first determined, and a peptide motif bound to site 3 mutant STX2B-subunit was then determined. Specifically, each of 2B and 2B-mutant (W32A) put on beads is prepared in an amount of from 3 to 5 mg, and filled in a column to prepare an affinity column.

Approximately 50 mg of a multiple peptide library for 1st screening: (MAXXXXA-AHA-)$_4$-3Lys is added and fully bound thereto. Thereafter, washing was conducted well with PBS or the like to wash out an unbound library.

Finally, the library put on the column is eluted with 30% acetic acid. The recovered fraction is dried up, and subjected to analysis of amino acid sequence. Consequently, numerical results of what amino acid is selected with what intensity are obtained. Normalization is conducted such that all the values of the 19 amino acids add up to 1.

The value of each amino acid in each degenerate position as obtained above when using 2B is divided by the value of each corresponding amino acid in each corresponding degenerate position as obtained above when using wild type: W32A. Consequently, how many times the amino acid in 2B is selected in comparison to the amino acid in W32A is a numerical value. That is, the binding motif specific to site 3 of STX2B-subunit can be determined by subtracting the selection ratio of each amino acid present in the former motif by the selection ratio of each corresponding amino acid present in the latter motif.

The other 18 amino acids are examined in the same manner, and normalization is finally conducted such that all the values of the 19 amino acids add up to 19. At this time, when there is no difference in selectivity between the amino acids, the value becomes 1. Generally, when this value exceeds 1.5, it is judged that a strong selectivity is observed. The results are shown in Table 1. Incidentally, in the following Tables 1 to 4 and FIGS. 6 and 7, amino acids are expressed by single character code.

TABLE 1

1st screening of the binding motif for 2B-subunit

| Degenerate position | | | |
|---|---|---|---|
| 1 | 2 | 3 | 4 |
| R (2.1) | | N (2.0) | |
| K (1.7) | R (1.8) | R (1.7) | R (1.8) |
| F (1.6) | K (1.7) | K (1.7) | K (1.8) |
| | N (1.7) | | N (1.6) |

On the basis of the resulting motif, the 2nd library shown in Table 2 was then prepared. In practice, amino acids such as Arg, Asn and Phe were selected in the 1st screening. Accordingly, these amino acids are introduced in the 2nd screening in fixed positions. Then, since the bindability to 2B-subunit as the overall library is increased, a more specific motif is easily obtained.

TABLE 2

Peptide libraries for the 2nd screening

Degenerate position 1234567
                     (MA-XXXXXXX-A-AHA)$_4$-3 Lys

XXRXNXX
                     XXXRXXX
                     XXXNXXX

Upon using the 2nd peptide libraries, a peptide motif bound to wild-type STX2B-subunit and a peptide motif bound to site 3 mutant STX2B-subunit were determined in the foregoing manner. The binding motif specific to site 3 of STX2B-subunit could be determined with a higher selectivity than the motif obtained using the 1st peptide library by dividing the selection ratio of each amino acid present in the former motif by the selection ratio of the corresponding amino acid present in the latter motif. The results are shown in Table 3.

TABLE 3

2nd screening of the binding motif for 2B-subunit

| Librar- | position | | | | | | |
|---|---|---|---|---|---|---|---|
| ies | 1 | 2 | 3 | 4 | 5 | 6 | 7 |
| R X N | P(1.5) | P(1.3) | R | R (1.4) | N | R(2.1) | R(3.0) |
|  |  | R(1.2) |  | I (1.3) |  | W(1.4) | W(1.4) |
| X R X | P(1.4) | P(1.4) | P(1.3) | R | R (1.5) | R(1.9) | R(2.3) |
|  | I(1.3) | I(1.2) | I(1.2) |  |  |  |  |
|  | W(1.2) | W(1.2) | W(1.2) |  |  |  |  |
|  | V(1.2) | V/I(1.2) | V/I(1.2) |  |  |  |  |
| X N X | K(1.7) | R(1.8) | R(1.8) | N | P (1.4) | R(1.8) | R/N(1.8) |
|  | R(1.6) | P(1.4) | N(1.5) |  | N(1.4) | N(1.4) | D(1.3) |
|  | P(1.5) | N(1.4) | P(1.4) |  | R (1.3) | D(1.3) |  |
|  | F(1.4) |  |  |  |  |  |  |

The amino acid sequences of the resulting peptide motifs are as follows.

(1)        FRRNRRN        (SEQ ID NO: 1)

(2)        PPPRRRR        (SEQ ID NO: 2)

(3)        PPRRNRR        (SEQ ID NO: 3)

(4)        KRRNPRR        (SEQ ID NO: 4)

Incidentally, with respect to motif (1) FRRNRRN (SEQ ID NO: 1), a basic amino acid and Pro, a hydrophobic amino acid are selected in the 2nd screening also. However, when an amino acid with the largest value in each position is withdrawn in the best motif, an information that a hydrophobic amino acid is preferable is not reflected. For this reason, Phe is introduced in the consensus sequence obtained in each library.

Thus, a compound was synthesized in which the resulting motif was incorporated into the molecular nuclear structure of the foregoing formula having three lysines (Lys) bound thereto as Met-Ala-Xo-Ala-AHA- (Xo represents any of the motifs, and AHA is as defined above).

In this instance, since the nuclear structure of Lys3 is commercially available in a state bound to beads, synthesis is conducted in sequence from the C terminal with a usual amino acid synthesizer, that is, four chains are extended at once in the formula of 3Lys. Since AHA has also an amino group and a carboxyl group, it is also possible to use the amino acid synthesizer.

Figure 5:
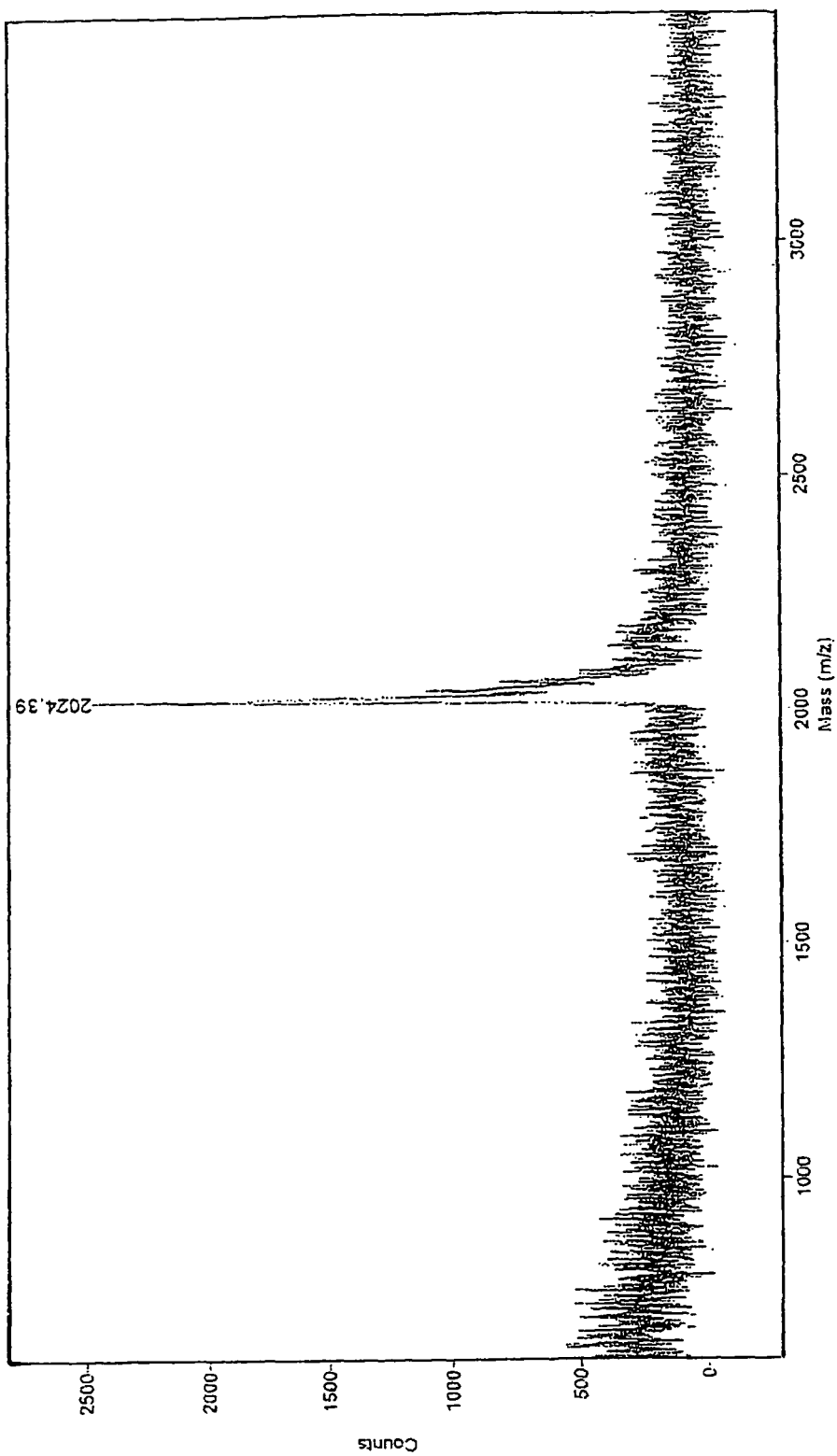
FIG. 5 is a mass spectrum of a peptide motif-free Met-Ala compound.

These compounds were identified by mass spectrometry. FIGS. 1, 2, 3 and 4 show mass spectrums of the foregoing peptide motifs (1), (2), (3) and (4). FIG. 5 shows a mass spectrum of a compound free of any of the peptide motifs, namely (Met-Ala):Met-Ala-Ala-AHA as a control.

<STX2 Inhibiting Peptide and Verotoxin Neutralizing Agent>

With respect to each of the foregoing compounds, the affinity for STX2B-subunit was examined, and the compound has been found to be bound thereto with a high affinity. It has been further found that the cytotoxicity of STX2 of vero cells is efficiently inhibited.

Figure 6:
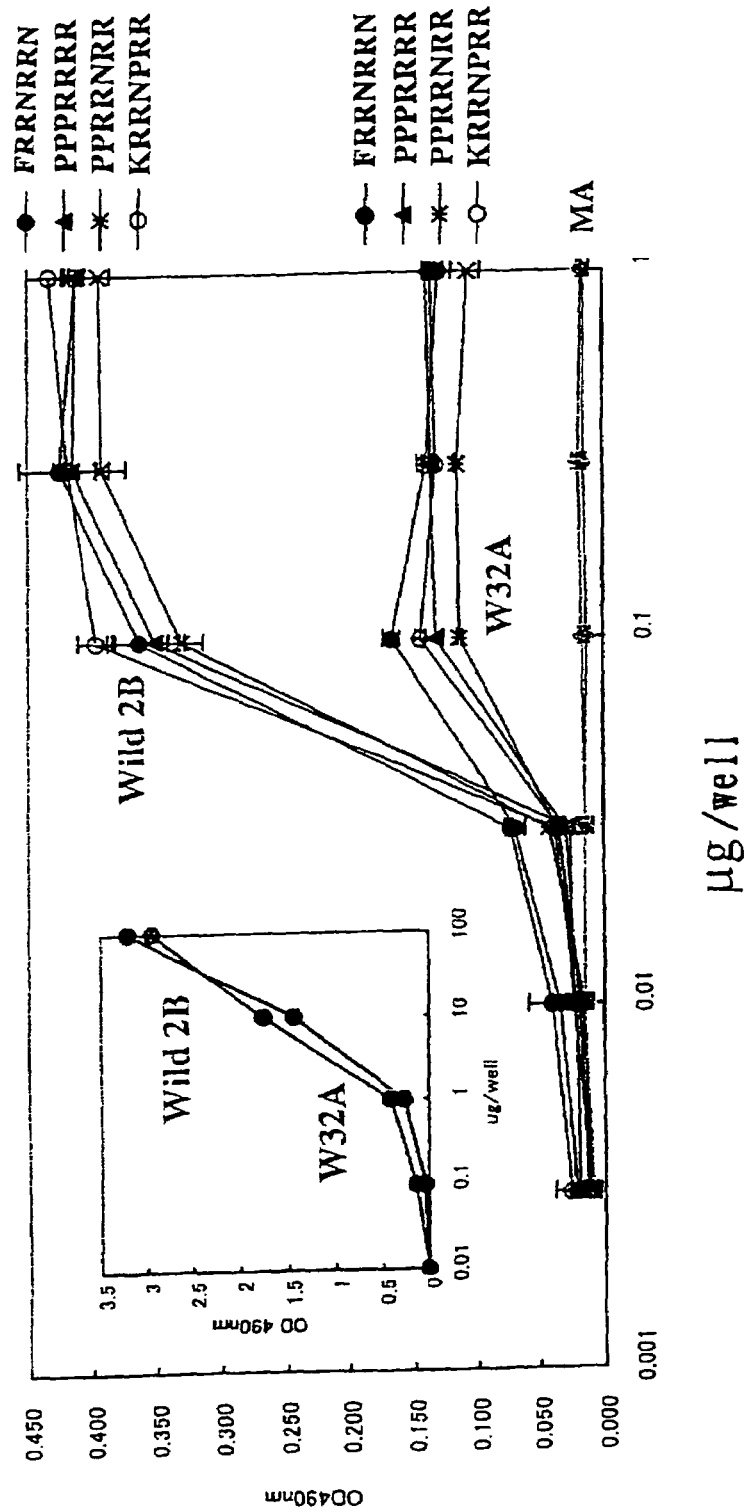
FIG. 6 is a graph showing an affinity for STX2B-subunit.

Table 4 and FIG. 6 show the affinity for STX2B-subunit. The measuring method is as follows.

That is, first, the synthetic peptide in an amount shown in FIG. 6 is coated on a plastic plate for ELISA. After blocking with 1% BSA, 0.1 microgram/ml of wild-type 2B-His or site 3 mutant W32A-His is added and bound thereto at room temperature for 1 hour. After washing, each 2B-subunit bound is detected by ELISA using anti-STX2 polyclonal antibody.

A small view in FIG. 6 shows that an anti-STX2 polyclonal antibody is likewise reacted with a known amount of wild-type 2B-His or site 3 mutant W32A-His.

Figure 7:
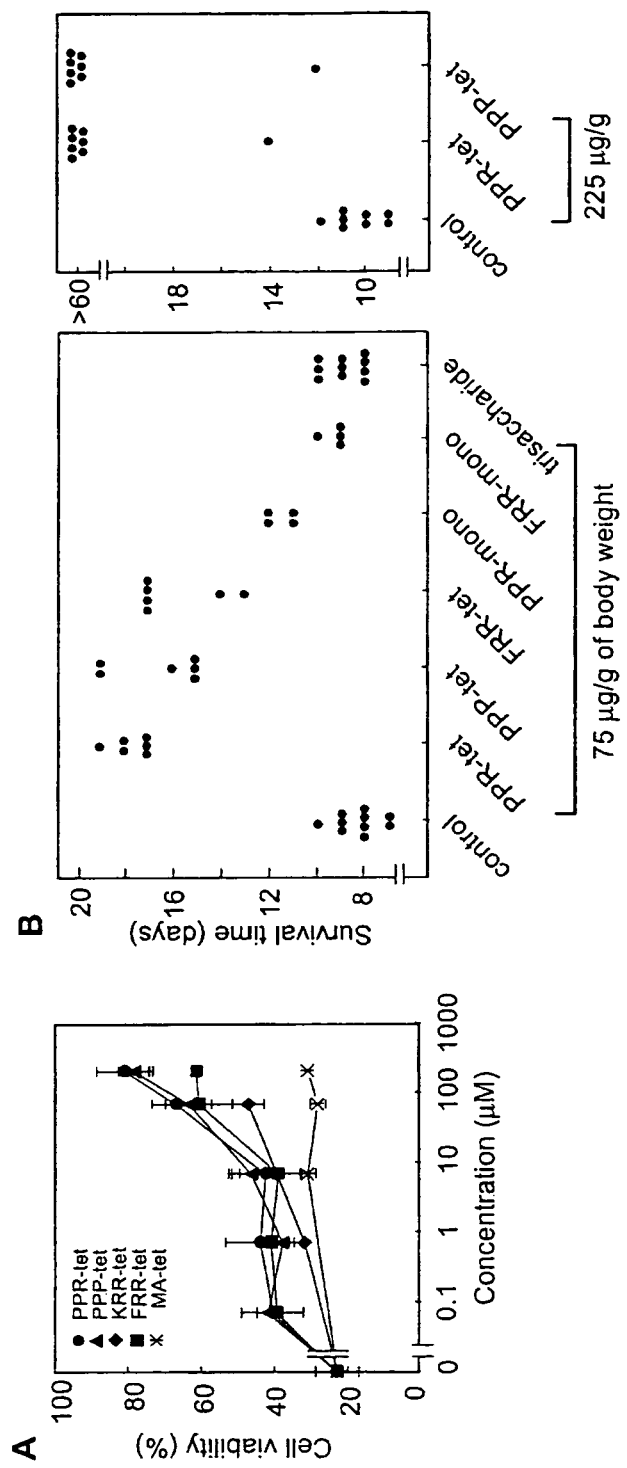
FIG. 7 is a graph showing an effect of inhibiting a cytotoxicity of STX2 of a vero cell.

FIG. 7A shows an effect of inhibiting an STX2 cytotoxicity of vero cells. In the measurement of the results in FIG. 7, 1 pg/ml of STX2 and each synthetic peptide at each concentration are caused to exist in cultured vero cells, and cultured for 3 days. Viable cells after the culturing are quantitatively determined by WST-assay (cell viability assay kit).

Values are shown on condition that a value in STX2(−) is defined as 100% and a value in 1 pg/ml of STX2 alone (namely, inhibitor-free) as 0%.

FIG. 7B shows the results of examination using a mouse infected with *E. coli* O157:H7. The procedure is as follows. That is, Day 0: A mouse deficient in protein calory was gastrically infected with a lethal dose of *E. coli* O157:H7N-9 strain. Day 2 to Day 4: A sample peptide, a trisaccharide analog (75 μg/g of body weight) or saline alone was gastrically administered twice a day. Day 2 to Day 5: PPR-tet or PPP-tet (225 μg/g of body weight) was gastrically administered twice a day.

The excellent functional effect of the sample peptide of this invention is confirmed.

MA indicated in FIGS. 6 and 7 refers to a control of reference compound (Met-Ala):Met-Ala-Ala-AHA which does not contain any of the foregoing peptide motifs (1), (2), (3) and (4) and whose mass spectrum is shown in FIG. 5. PPR-tet and the like indicated in FIG. 7 correspond to those shown in Table 4.

TABLE 4

Kinetic analysis of the binding of synthetic Peptides to His-tagged Stx 2B-subunit

|  | $K_D$ (μm of unit) | $RU_{max}$ (AU) | SEQ ID NO: |
|---|---|---|---|
| PPRRNRR | 2.7 | 1,350 | 3 |
| PPPRRRR | 3.2 | 1,250 | 2 |
| KRRNPRR | 2.1 | 1,290 | 4 |
| FRRNRRN | 1.7 | 1,490 | 1 |
| MA | ND | ND |  |
| SUPER TWIG(1)$_4$6 | 1.1 | 640 |  |

In the above-described compounds, AHA (aminohexanoic acid) is used as the spacer molecule, and Ala present between AHA and peptide motif Xo and Met-Ala as a terminal modification molecule of peptide motif Xo are introduced for confirming the amino acid sequencing. These may be various types. AHA as the spacer molecule is one selected from the comparative examination with SUPER TWIG as a substance containing an amino group and a carboxyl group and having a chain length of 6 carbon atoms. Although the carbon number is preferably 6, it may be from 4 to 10.

As the spacer molecule, other types of molecules are also available unless impairing the activity of inhibiting STX2 with peptide motif Xo and molecular nuclear structure portion 3Lys.

Terminal Met-Ala and Ala bound to AHA introduced for amino acid sequencing at the time of screening may be other appropriate amino acids. After the screening, these are unnecessary because of lack of the activity of inhibiting STX2. However, when $NH_2$ is exposed to the terminal of the motif, a plus charge is provided. From the standpoint of controlling the charge, it is preferable that terminal MA or other types are present. These are generally uncharged amino acids, and preferably amino acids which have no great influence on hydrophobicity.

In this case, various modifications and the like may be taken into consideration.

For example, it is considered that $NH_2$ of Met in the N-terminal is protected with an acetyl group for stabilization to suppress gastrointestinal decomposition with a protease which is caused by oral administration.

According to the inventors' confirmation, the acetylation increases the function (activity) of inhibiting the in-vivo cytotoxicity of STX2 by approximately five times. In the infection experiment as well, the increase in effect is confirmed.

From the foregoing as well, for example, (acetyl-Xo-AHA)$_4$3Lys, replacement of acetyl with another protecting group, replacement of AHA with another spacer or the absence of the spacer is advantageously considered.

According to the inventors' investigations, with respect to the STX2 inhibiting peptide provided by the foregoing screening method, various variations have been further found for exhibiting its activity.

That is, it has been found more commonly that the STX2 inhibiting peptide is considered a peptide in which a peptide motif which is formed by peptide linkage of at least seven amino acids, whose sequence has two cluster portions each having bound thereto at least two basic amino acids, for example, asparagine (Arg), lysine (Lys) and histidine (His)

and whose C-terminal side is a basic amino acid is incorporated in a molecular nuclear structure portion having three molecules of lysine (Lys) peptide-linked thereto.

Among others, it is considered preferable that arginine (Arg) is contained as the basic amino acid constituting the cluster portion. Accordingly, a preferable cluster portion is, for example, -Arg-Arg- or -Arg-Arg-Asn-.

In the STX2 inhibiting peptide of this invention, it is preferable that the C-terminal side is a basic amino acid, for example, arginine (Arg) and the N-terminal side is a hydrophobic amino acid, for example, proline (Pro).

The reason for the C-terminal side being preferably the basic amino acid is considered to be that the acidic amino acid cluster is present near globo3 sugar binding site 3 of STX2B-subunit to be bound and both statically interact to increase the affinity. The reason for the N-terminal side being preferably the hydrophobic amino acid is considered to be that it hydrophobically interacts with tryptophan (Trp) which plays a main role in globo3 sugar binding site 3 of STX2B-subunit.

In view of the foregoing, motifs (1), (2), (3) and (4) are provided in this invention as a preferable example.

The peptide motif in this invention comprises at least seven amino acids as described above in consideration of the molecular size effect on the STX2 inhibiting function. However, the number of amino acids may be more than 7 unless the STX2 inhibitory activity is greatly impaired, and the larger number of amino acids is available for application to drugs or the like. Further, needless to say, various spacers or terminal modification groups may be provided as stated above.

In this invention, as the verotoxin neutralizing agent containing the peptide having the STX2 inhibitory activity as an active ingredient, various dosage forms may be employed. In the oral administration, the agent may be formulated with a vehicle and the like to provide tablets or a powder, or a liquid preparation as a composition with purified water and the like. In the composition and the dosage forms, various ingredients including known ones may be used. Various methods may be employed for this purpose.

Regarding the dose as the verotoxin neutralizing agent, it may be considered to be used generally at a dose of from 5 to 500 mg/kg-body weight since the discovery of the infection with *E. coli* O157:H7. Of course, it may properly be determined according to the symptom.

In recent years, a large number of peptides having a high physiological activity in trace amounts have been discovered, and supply of peptides in large quantities has been enabled by the rapid progress of biotechnologies such as gene recombination technology and cell fusion. Attempts have been made to apply these physiologically active peptides to therapy of diseases as pharmaceutical preparations. It has been however known that even though such peptide pharmaceutical preparations are orally administered, no sufficient absorption ratio is obtained. This is presumably because these peptide pharmaceutical preparations undergo rapid decomposition with a digestive enzyme or a protease in the digestive tract or less permeate the mucous membrane of the digestive tract owing to water solubility and high molecular weight. For this reason, the administration of these pharmaceutical preparations is mostly limited clinically to the administration by injection such as muscular administration, subcutaneous administration or intravenous administration. However, these administrations by injection have defects that they give pains to patients and severe side effects such as allergic reaction and anaphylactoid shock are developed. Accordingly, permucosal administration including oral administration has lately attracted much interest as an administration route to replace the injection. However, no sufficient absorption ratio is obtained in comparison to the injection. Therefore, at present, for improving the absorption ratio of physiologically active peptides after oral administration and permucosal administration, various methods have been attempted. These can be classified in (1) use of pharmaceutical additives such as an absorption enhancer and a protease inhibitor, (2) development of a new administration route of drugs, (3) modification of a molecular structure of drugs and (4) dosage form modification of drugs.

In this invention as well, in the actual administration of drugs, various embodiments based on the past technical knowledge can be employed for enabling the oral administration. For example, it is possible to adopt appropriate approaches, for example, use of typical surfactants, bile acid, chelating agents and hydrocarbons such as fatty acids as an absorption enhancer, addition of sodium glycocholate, bacitracin, soybean trypsin inhibitor, camostat, aprotinin and the like as a protease inhibitor, inclusion in liposome or emulsion and use by encapsulation.

INDUSTRIAL APPLICABILITY

According to the method of this invention, it is possible, as stated above, to screen the toxin neutralizing peptides which have the property of inhibiting toxins with the receptor binding portion having the subunit structure, such as verotoxin, cholera toxin, pertussis toxin and toxin of *Bacillus anthracis*, whose synthesis is easy as peptide synthesis and which are effective as a therapeutic agent, and to provide these peptides.

The foregoing peptides of this invention have the STX2 inhibiting property, are easy to synthesize as peptide synthesis, and can provide the verotoxin neutralizing agent which is effective as a therapeutic agent of enterohemorrhagic *Escherichia coli* infectious diseases.

The invention claimed is:

1. A method for screening for a tetravalent peptide which can neutralize a Shiga Toxin 2 toxin, the method comprising:
   (a) providing a wild-type Shiga Toxin 2 (STX2) toxin comprising a plurality of subunits and having a receptor-binding site;
   (b) providing a mutant of said wild type STX2 toxin having a mutation in the receptor-binding site which decreases the affinity of the mutant for a receptor of the toxin as compared to the affinity of the wild type STX2 toxin;
   (c) providing a first tetravalent peptide library comprising a plurality of members, each member comprising a core structure consisting of the following structure of three bound lysines, $$\begin{array}{c}
-NH \\
\diagdown \\
(CH_2)_4 \\
\diagdown \\
CH-CONH-CH-(CH_2)_4-NHCO-CH \\
\diagup \qquad\qquad | \qquad\qquad\qquad\qquad\qquad \diagup \\
-NH \qquad\qquad CO \qquad\qquad\qquad\qquad NH- \\
\qquad\qquad\qquad | \\
\qquad\qquad\qquad OH
\end{array} \begin{array}{c} NH- \\ \diagup \\ (CH_2)_4 \\ \diagup \\ \\ NH- \end{array}$$

and four identical degenerate peptides having randomized amino acids in a plurality of degenerate positions bound to each terminal amino group of the core structure, wherein the degenerate peptides have a structure selected from the group consisting of:

[terminal modification molecule]-Xaa-Xaa-Xaa-Xaa-A-AHA, and
[terminal modification molecule]-Xaa-Xaa-Xaa-Xaa-Xaa-Xaa-Xaa-A-AHA,
where the terminal modification molecule consists of one or more uncharged amino acids, Xaa is a degenerate position signifying any naturally occurring amino acid, A is alanine, and AHA is aminohexanoic acid;
(d) contacting said first tetravalent peptide library with the wild type STX2 toxin and the mutant wild type STX2 toxin;
(e) determining wild-type peptide motifs within the plurality of members that bind to the wild type STX2 toxin;
(f) determining mutant peptide motifs within the plurality of members that bind to the mutant wild type STX2 toxin;
(g) determining the amino acid sequences of the wild-type peptide motifs of step (e) and assigning first normalized values for the occurrence of each amino acid at each degenerate position in the wild-type peptide motifs so that the sum of the first normalized values at each degenerate position for all amino acids occurring in the degenerate position equals 1;
(h) determining the amino acid sequences of the mutant peptide motifs of step (f) and assigning second normalized values for the occurrence of each amino acid at each degenerate position in the mutant peptide motifs so that the sum of the second normalized values at each degenerate position for all amino acids occurring in the degenerate position equals 1;
(i) dividing each of the first normalized values for each of the amino acids at each position by the corresponding second normalized values and obtaining a selection ratio for each amino acid in each degenerate position of the peptide motifs of steps (e) and (f); and
(j) obtaining a tetravalent peptide which can neutralize the STX2 toxin by selecting a tetravalent peptide comprising the core structure and four identical peptides bound to each terminal amino group of the core structure, wherein the four identical peptides comprise amino acids at positions corresponding to the degenerate positions of the degenerate peptides having a selection ratio greater than 1.5 as determined in step (i).

2. The method according to claim 1, wherein a second tetravalent peptide library is also applied in steps (d) to (j), and wherein the second tetravalent peptide library comprises four identical peptides of step (j) in order to obtain a receptor-binding site-specific peptide motif with a higher selectivity for the receptor.

3. The method according to claim 1, wherein in the first tetravalent peptide library, the degenerate peptides are bound to the terminal amino groups of the core structure via spacer molecules.

4. The method according to claim 2, wherein in the first tetravalent peptide library, the degenerate peptides are bound to the terminal amino groups of the core structure via spacer molecules.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial
<220> FEATURE:
<223> OTHER INFORMATION: Synthetic oligopeptide

<400> SEQUENCE: 1

Phe Arg Arg Asn Arg Arg Asn
1               5
```

```
<210> SEQ ID NO 2
<211> LENGTH: 7
<212> TYPE: PRT
<213> ORGANISM: Artificial
<220> FEATURE:
<223> OTHER INFORMATION: Synthetic oligopeptide

<400> SEQUENCE: 2

Pro Pro Pro Arg Arg Arg Arg
1               5

<210> SEQ ID NO 3
<211> LENGTH: 7
<212> TYPE: PRT
<213> ORGANISM: Artificial
<220> FEATURE:
<223> OTHER INFORMATION: Synthetic oligopeptide

<400> SEQUENCE: 3

Pro Pro Arg Arg Asn Arg Arg
1               5

<210> SEQ ID NO 4
<211> LENGTH: 7
<212> TYPE: PRT
<213> ORGANISM: Artificial
<220> FEATURE:
<223> OTHER INFORMATION: Synthetic oligopeptide

<400> SEQUENCE: 4

Lys Arg Arg Asn Pro Arg Arg
1               5

<210> SEQ ID NO 5
<211> LENGTH: 8
<212> TYPE: PRT
<213> ORGANISM: Artificial
<220> FEATURE:
<223> OTHER INFORMATION: Synthetic oligopeptide
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Aminohexanoic acid

<400> SEQUENCE: 5

Met Ala Xaa Xaa Xaa Xaa Ala Xaa
1               5
```